(12) United States Patent
Takahashi et al.

(10) Patent No.: US 6,740,529 B2
(45) Date of Patent: May 25, 2004

(54) DISPENSING APPARATUS

(75) Inventors: Katsuaki Takahashi, Hitachinaka (JP); Hajime Yamazaki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 451 days.

(21) Appl. No.: 09/789,592

(22) Filed: Feb. 22, 2001

(65) Prior Publication Data

US 2002/0006668 A1 Jan. 17, 2002

(30) Foreign Application Priority Data

Jul. 11, 2000 (JP) .................................. 2000-210435

(51) Int. Cl.[7] .............................. G01N 1/00; G01N 1/10; G01N 31/00; B01L 3/02; G05B 21/00
(52) U.S. Cl. ..................... 436/179; 436/174; 436/179; 422/100; 422/63; 422/67; 422/81; 700/266
(58) Field of Search ..................... 436/179, 174, 436/180; 700/266; 422/81, 100, 63–68.1, 73

(56) References Cited

U.S. PATENT DOCUMENTS

| | | | | | |
|---|---|---|---|---|---|
| 3,609,069 A | * | 9/1971 | Martinelli | ..................... | 417/474 |
| 4,108,608 A | * | 8/1978 | Maher et al. | ............. | 73/864.12 |
| 4,231,990 A | * | 11/1980 | Jottier | ......................... | 422/100 |
| 4,244,919 A | * | 1/1981 | Chen | ............................ | 422/100 |
| 4,369,664 A | * | 1/1983 | Bunce et al. | ............. | 73/864.12 |
| 4,552,516 A | * | 11/1985 | Stanley | ................... | 417/477.11 |
| 5,395,588 A | * | 3/1995 | North et al. | .................... | 422/81 |
| 5,679,575 A | * | 10/1997 | Kubota et al. | .................. | 436/49 |
| 5,789,252 A | * | 8/1998 | Fujita et al. | ................... | 436/49 |
| 5,827,480 A | * | 10/1998 | Haff et al. | .................. | 422/68.1 |
| 5,833,925 A | * | 11/1998 | Shu et al. | ..................... | 422/63 |
| 5,853,665 A | * | 12/1998 | Ade et al. | ..................... | 422/62 |
| 5,879,629 A | * | 3/1999 | Capuano et al. | .............. | 422/82 |
| 5,993,744 A | * | 11/1999 | Rao et al. | .................... | 422/103 |
| 6,040,186 A | * | 3/2000 | Lewis et al. | ................... | 436/53 |
| 6,066,298 A | * | 5/2000 | Fukunaga | .................... | 422/100 |
| 6,365,107 B1 | * | 4/2002 | Markelov et al. | ............. | 422/83 |
| 6,387,328 B1 | * | 5/2002 | Berndtsson | ................... | 422/73 |
| 6,474,144 B1 | * | 11/2002 | Barnes et al. | .............. | 73/61.71 |
| 6,576,477 B1 | * | 6/2003 | Tokiwa et al. | .............. | 436/180 |
| 2002/0064481 A1 | * | 5/2002 | Ishizawa et al. | .............. | 422/64 |
| 2002/0064880 A1 | * | 5/2002 | Merten et al. | .................. | 436/43 |
| 2002/0098122 A1 | * | 7/2002 | Singh et al. | ................. | 422/100 |
| 2002/0192113 A1 | * | 12/2002 | Uffenheimer et al. | ......... | 422/67 |
| 2003/0013199 A1 | * | 1/2003 | Anderson et al. | ............. | 436/50 |

FOREIGN PATENT DOCUMENTS

JP  11-230970  8/1999

* cited by examiner

*Primary Examiner*—Jill Warden
*Assistant Examiner*—Brian R Gordon
(74) *Attorney, Agent, or Firm*—Mattingly, Stanger & Malur, P.C.

(57) ABSTRACT

A diluting solution moving unit moves a diluting solution in forward and reverse directions in a flow path. A probe is connected to the flow path through a T-junction and sucks a sample. A sample syringe is connected to the flow path through a T-junction. A control unit performs controlling so that the diluting solution moving unit is driven to move the diluting solution in the flow path and the sample syringe is driven to make the probe suck the sample into the flow path to thereby dilute the sucked sample with the diluting solution and further driven so that the sample solution diluted with the diluting solution is delivered from the probe into any one of reaction containers. There can be provided a dispensing apparatus in which dilution of the sample is made in a short time and in which the accuracy of the diluting rate is improved.

7 Claims, 3 Drawing Sheets

DISPENSING APPARATUS

BACKGROUND OF THE INVENTION

1. Field of the Invention

The present invention relates to a dispensing apparatus for quantitatively dispensing blood, urine, etc. and particularly to a dispensing apparatus adapted for diluting and dispensing blood, urine, etc.

2. Description of the Related Art

In an automatically analyzing apparatus, analysis items in a vital sample such as blood, urine, etc. are analyzed by using a dispensing apparatus in such a manner as follows. The vital sample is dispensed into reaction containers on a reaction line. The sample is made to react with a reaction reagent in each of the reaction containers. A reaction solution produced as a result of the reaction is measured, for example, optically. In this manner, analysis items in the sample are analyzed. In the automatically analyzing apparatus, various reaction reagents are used in accordance with a large number of analysis items. To reduce the running cost of such inspection work, it is necessary to reduce the quantity of use of each reaction reagent.

To keep the range of measurement in the same concentration as obtained before the quantity of the reagent is reduced, the quantity of the sample needs to be reduced in the same rate as the quantity of the reagent is reduced. When, for example, the quantity of the reagent is reduced to half, the quantity of the sample is also reduced to half so that the concentration of the sample relative to the reagent is kept constant.

Two methods have been heretofore used for reducing the quantity of the sample. In one of the methods, the sample is diluted, while in the other of methods, the quantity of dispensation per se is reduced. The terminology "dilution" will be described upon the case where the sample is diluted by 10 times by way of example. When 1 $\mu$l of an undiluted sample is dispensed, 9 $\mu$l of a diluting solution is added to the undiluted sample so that the undiluted sample is diluted by 10 times. That is, 10 $\mu$l of a diluted sample solution is prepared. Out of 10 $\mu$l, 2 $\mu$l of the diluted sample solution is dispensed into each reaction container. (In this case, the dilution is equivalent to about 5-fold dilution.) On the other hand, in the method of reducing the quantity of dispensation per se, the minimum quantity of dispensation is limited to about 1 $\mu$l. If the quantity is reduced to be smaller than about 1 $\mu$l, reproducibility is lowered.

For example, as the background-art sample diluting method, a method disclosed in JP-A-11-230970 is known. In the method, a sample is sucked into a probe by a sample syringe while a diluting solution is made to flow by using a diluting syringe. Hence, both the suction and dilution of the sample are performed simultaneously. The diluted sample is delivered into each reaction container by using the sample syringe. In the method, the sample can be diluted without use of any dilution exclusive line. Hence, efficient dilution and dispensation can be made in a short time.

In the method described in JP-A-11-230970, it is, however, necessary that the size of the sample syringe is selected to be larger than the size of the diluting syringe. This is because the diluting syringe is required to feed out only a predetermined amount of the diluting solution, while the sample syringe is required to suck a predetermined amount of the sample in addition to the diluting solution fed out by the diluting syringe. Accordingly, the size (flow quantity) of the sample syringe becomes larger than that of the diluting syringe. The fact that the syringe becomes larger means that the plunger diameter of the syringe becomes larger. That is, it is necessary that the plunger diameter of the sample syringe is selected to be larger than that of the diluting syringe. If the plunger diameter becomes larger, the accuracy in the quantity of suction of the sample is worsened. Hence, there is a problem that the accuracy of the diluting rate is deteriorated.

SUMMARY OF THE INVENTION

An object of the present invention is to provide a dispensing apparatus in which a sample can be diluted in a short time and in which the accuracy of the diluting rate is improved.

(1) In order to achieve the above object, according to the present invention, there is provided a dispensing apparatus comprising: a diluting solution moving means for moving a diluting solution in a flow path in forward and reverse directions; a probe connected to the flow path through a junction and capable of sucking a sample; a sample syringe connected to the flow path through a junction; and a control means for controlling operations of the diluting solution moving means and the syringe, whereby the control means performs controlling so that the diluting solution moving means driven to move the diluting solution in the flow path and the syringe is driven to make the probe suck sample into the flow path to thereby dilute the sucked sample with the moved diluting solution, and the syringe is further driven so that the sample solution diluted with the diluting solution is delivered from the probe into a reaction container.

By such a configuration, the sample can be diluted in a short time and the accuracy of the diluting rate can be improved.

(2) In the above item (1), preferably, the above control means performs control so that the sample syringe is operated to deliver a high-concentration sample out of the probe into a washing bath before the diluted sample solution is discharged from the probe by the sample syringe.

(3) In the above item (1), preferably, the above control means performs control so that the sample syringe is operated to move the diluting solution in the flow path in a direction opposite to a direction of movement of the diluting solution at the time of dilution of the sample to thereby move the sample diffused in the flow path before the diluted sample solution is discharged from the probe by the sample syringe.

By such a configuration, diluting error can be reduced.

(4) In the above item (1), preferably, the diluting solution moving means includes: a first syringe connected to an end portion of the flow path; a second syringe connected to the other end portion of the flow path; and a drive means for driving plungers of the first and second syringes; wherein the first and second syringes operate so that the second syringe discharges the diluting solution in the flow path when the first syringe sucks the diluting solution in the flow path, and that the second syringe sucks the diluting solution in the flow path when the first syringe discharges the diluting solution in the flow path, the quantity of suction by the first syringe being equal to the quantity of delivery by the second syringe.

(5) In the above item (1), preferably, the above diluting solution moving means includes: a plurality of rollers for squashing a tube connected to opposite ends of the flow path; and a drive means for driving the rollers to rotate in forward and reverse directions.

DETAILED DESCRIPTION OF THE EMBODIMENTS

The configuration and operation of a dispensing apparatus according to a first embodiment of the present invention will be described below with reference to FIGS. 1 and 2.

Figure 1:
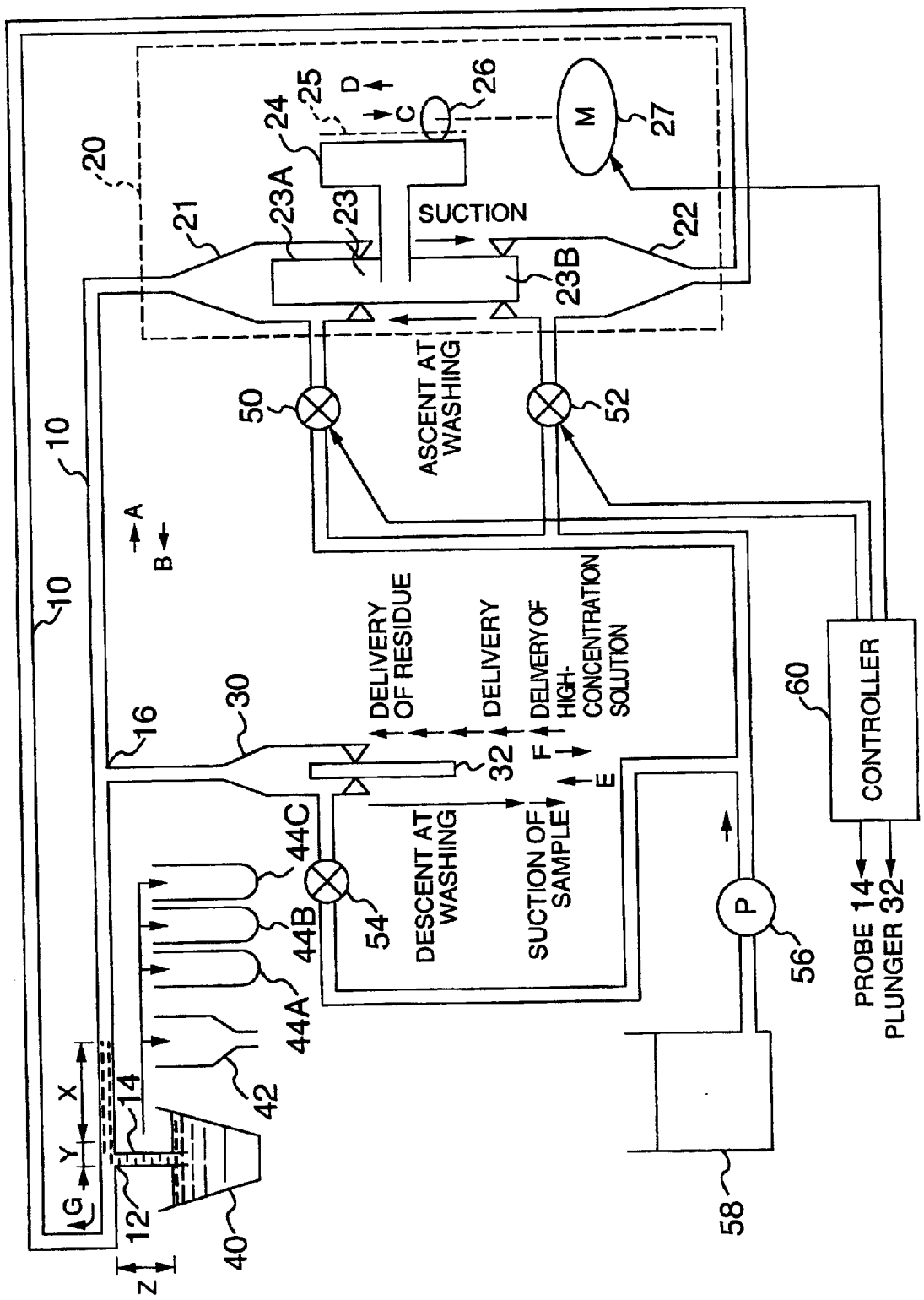
FIG. 1 is a system block diagram showing the configuration of a dispensing apparatus according to a first embodiment of the present invention.

Referring to FIG. 1, the configuration of the dispensing apparatus according to this embodiment will be described first.

FIG. 1 is a system block diagram showing the configuration of the dispensing apparatus according to the first embodiment of the present invention.

Opposite end portions of a flow path 10 are connected to a diluting solution moving means 20 to thereby form a closed flow path. The diluting solution moving means 20 moves a diluting solution in the closed flow path 10 in each of reverse directions, that is, in the direction of the arrow A or in the direction of the arrow B opposite to the direction of the arrow A. As will be described later, when a sample is introduced into the flow path 10, the introduced sample is diluted with a diluting solution to thereby form a diluted sample solution. The diluted sample solution is also moved in the flow path 10 by the diluting solution moving means 20. The diluting solution moving means 20 has diluting solution moving syringes 21 and 22, a plunger 23, a slider 24, a rack 25, a pinion 26, and a drive motor 27. The plunger 23 has plunger portions 23A and 23B at its opposite ends respectively. The plunger portion 23A is inserted into the diluting solution moving syringe 21. The plunger portion 23B is inserted into the diluting solution moving syringe 22. The rack 25 is attached to the slider 24 engaged with the plunger 23. The pinion 26 driven to rotate by the drive motor 27 is engaged with the rack 25. When the pinion 26 is driven to rotate by the drive motor 27, the slider 24 and the plunger 23 are driven to move in the direction of the arrow C and in the direction of the arrow D respectively. When the plunger 23 moves in the direction of the arrow C, the diluting solution moving syringe 21 performs a sucking operation and, at the same time, the diluting solution moving syringe 22 performs a delivering operation. Because the quantity of suction by the diluting solution moving syringe 21 is equal to the quantity of delivery by the diluting solution moving syringe 22, the fluid (diluting solution) in the closed flow path 10 moves in the direction of the arrow A. When the plunger 23 moves in the direction of the arrow D, the diluting solution moving syringe 21 performs a delivering operation and, at the same time, the diluting solution moving syringe 22 performs a sucking operation. As a result, the diluting solution in the closed flow path 10 moves in the direction of the arrow B.

A probe 14 is attached to the closed flow path 10 through a T-junction 12. The probe 14 can move among a sample container 40, a washing bath 42 and reaction containers 44A, 44B and 44C. When a tip of the probe 14 is inserted into the sample container 40, the sample is sucked. When the tip of the probe 14 is inserted into the washing bath 42, a washing solution is sucked. When the probe 14 is further moved to the reaction containers 44A, 44B and 44C, the sample diluted with the diluting solution is delivered. Although the above description has been made upon the case where the diluted sample is dispensed into three reaction containers 44A, 44B and 44C, the number of reaction containers assigned for the diluted sample is not limited to three.

A sample syringe 30 is disposed in the flow path 10 between the T-junction 12 and the diluting solution moving syringe 21 through a T-junction 16. The sample syringe 30 has a plunger 32. When the plunger 32 moves in the direction of the arrow F, the sample can be sucked from the sample container 40. When the plunger 32 moves in the direction of the arrow E, the diluted sample can be delivered into the reaction containers 44 (44A, 44B and 44C).

Electromagnetic valves 50, 52 and 54 are connected behind the diluting solution moving syringes 21 and 22 and the sample syringe 30 respectively. The electromagnetic valves 50, 52 and 54 are connected to the diluting solution tank 58 through a pump 56. The diluting solution is reserved in the diluting solution tank 58. For example, pure water is used as the diluting solution. The diluting solution is used for washing the probe 14 as well as for diluting the sample.

A control portion 60 controls forward rotation, reverse rotation and suspension of the drive motor 27, reciprocating motion of the plunger 32, opening and closing of the electromagnetic valves 50, 52 and 54 and horizontal and vertical movement of the probe 14.

The operation of the dispensing apparatus according to this embodiment will be described below with reference to FIGS. 1 and 2.

Figure 2:
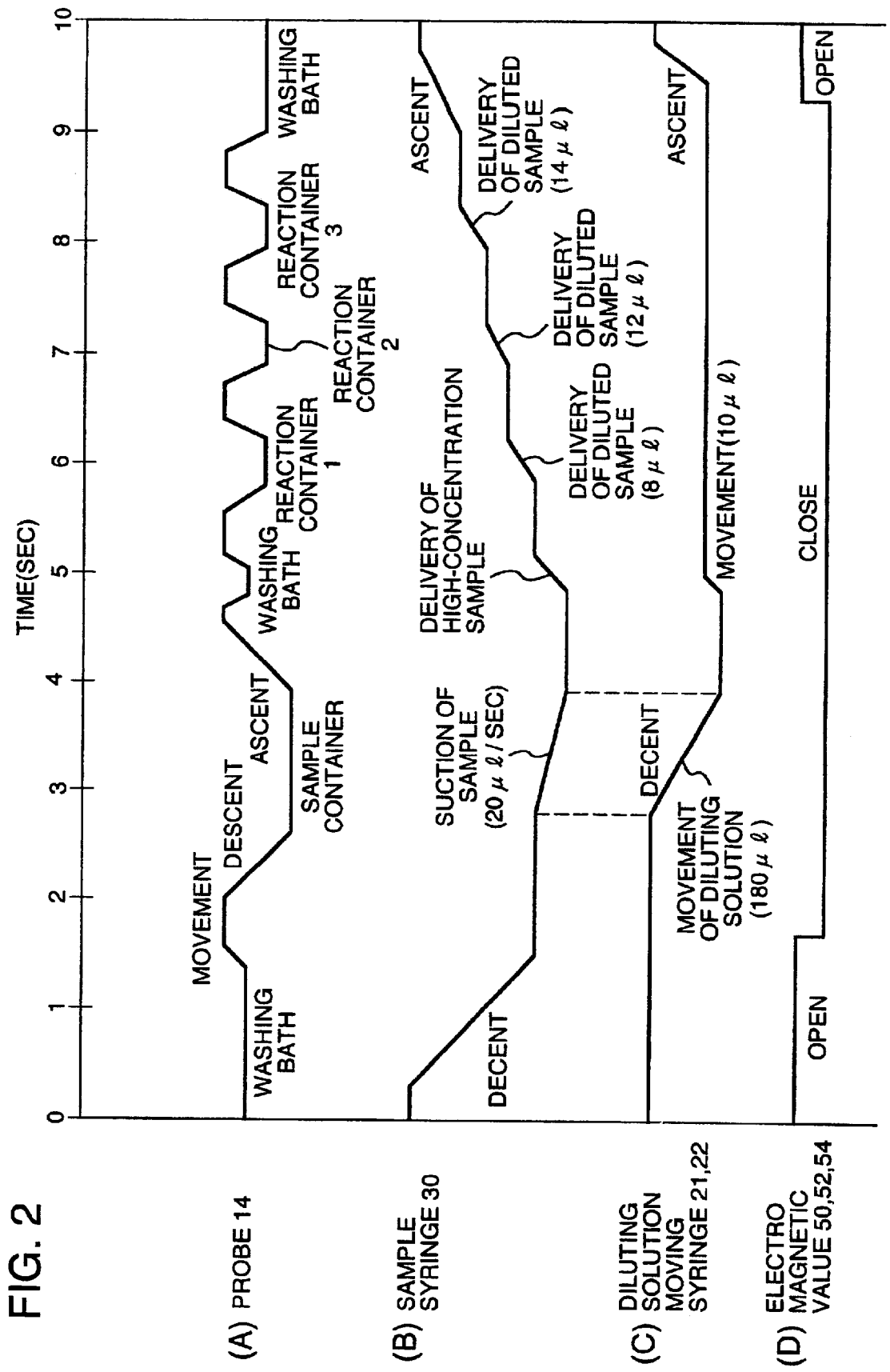
FIG. 2 is a time chart showing the operation of the dispensing apparatus according to the embodiment of the present invention.

FIG. 2 is a time chart showing the operation of the dispensing apparatus according to an embodiment of the present invention. In FIG. 2, the vertical axis (A) shows the operation of the probe 14. In FIG. 2, the vertical axis (B) shows the operation of the sample syringe 30. In FIG. 2, the vertical axis (C) shows the operation of the diluting solution moving syringes 21 and 22. In FIG. 2, the vertical axis (D) shows the operation of the electromagnetic valves 50, 52 and 54. In FIG. 2, the horizontal axis shows the elapsed time. The operation for one cycle is completed in a period of from a point of time of 0 sec to a point of time of 10 sec.

The initial operation will be described first. At a point of time of 0 sec, the control portion 60 moves the probe 14 so that the probe 14 is positioned above the washing bath 42 as shown in the diagram (A) of FIG. 2. As shown in the diagrams (B) and (C) of FIG. 2, the control portion 60 moves up the plungers 23A and 32 to their upper limits respectively. At the point of time of 0 sec, the control portion 60 opens the electromagnetic valves 50, 52 and 54 so that the flow path 10 is filled with the diluting solution as shown in the diagram (D) of FIG. 2. The diluting solution is delivered from the tip of the probe 14 into the washing bath 42. Thus, the initial preparatory operation is completed.

The operation in a period of from a point of time of 0 sec to a point of time of 1.5 sec will be described next.

When the probe 14 is positioned in the washing bath 42, the control portion 60 opens the electromagnetic valve 54 and moves down the plunger 32 of the sample syringe 30 as shown in the diagram (B) of FIG. 2 while pouring water from the probe 14 into the washing bath 42. Because the quantity of the diluting solution delivered by the pump 56 is larger than the quantity of suction caused by the descent of the plunger 32, the diluting solution is still delivered from the tip of the probe 14.

The quantity of descent of the plunger 32 is determined according to the following expression:

Descent $Vs = V1+V2+V3+$(the quantity of pressing the undiluted solution from the probe) $Vp+$(the dummy quantity of the residual solution) $Vd$     (1)

in which V1 is the quantity of the diluted sample dispensed into the reaction container 44A, V2 is the quantity of the diluted sample dispensed into the reaction container 44B, and V3 is the quantity of the diluted solution dispensed into the reaction container 44C.

Assume now that the quantity (virtual quantity) Va1 of the undiluted sample to be dispensed into the reaction container 44A is 0.8 $\mu$l, the quantity (virtual quantity) Va2 of the undiluted sample to be dispensed into the reaction container 44B is 1.2 $\mu$l, and the quantity (virtual quantity) Va3 of the undiluted sample to be dispensed into the reaction container 44C is 1.4 $\mu$l. When, for example, the rate of diluting is 10, the quantity V1 of the diluted sample dispensed into the reaction container 44A is 8 $\mu$l, the quantity V2 of the diluted sample dispensed into the reaction container 44B is 12 $\mu$l, and the quantity V3 of the diluted sample dispensed into the reaction container 44C is 14 $\mu$l.

Assuming now that the length of from the tip of the probe 14 to the junction 12 is 10 mm and the inner diameter of the probe 14 is 0.4 mm$\varnothing$, then the volume Vb of the probe is as follows.

$$Vb = (\pi \times 0.4 \times 0.4)/4 \times 10 = 1.256 \, \mu l$$

The quantity Vp of pressing the undiluted sample out of the probe is the quantity of entirely replacing the undiluted sample with the diluted sample in the probe 14. That is, the quantity VP is the quantity of entirely replacing the concentration of the undiluted sample with the concentration of the diluted sample. Hence, the quantity Vp needs to be about 15 times as large as the volume Vb of the probe 14. Accordingly:

$$Vp = 1.256 \times 15 = 18.84 \approx 19 \, \mu l$$

When the diluted solution flows in the flow path 10 (diluting mixing pipe) between the T-junctions 12 and 16, the diluted solution may be further diluted by diffusion in the boundary portion between the diluting solution and the diluted sample. To solve this problem, a part of the diluted sample is provided as a dummy solution, so that the dummy solution is not used for analysis. The quantity of the dummy solution is the dummy quantity Vd of the residual solution. The dummy quantity Vd of the residual solution is affected by the quantity of movement of the diluted solution in the diluting mixing pipe, the rate of movement thereof, the diameter of the pipe, the diffusion coefficient, etc. For example, Vd of 30 $\mu$l is sufficient.

Accordingly, the quantity of descent Vs is given as follows.

$$Vs = 8+12+14+19+30 = 83 \, \mu l$$

When the quantity Vs of descent of the plunger 32 of the sample syringe 30 is completed, the control portion 60 closes the electromagnetic valves 50, 52 and 54 as shown in the diagram (D) of FIG. 2.

The operation in a period of from a point of time of 1.5 sec to a point of time of 3.8 sec will be described next.

As shown in the diagram (A) of FIG. 2, the control portion 60 moves the probe 14 to the position of the sample container 40 and further moves down the probe 14 into the sample container 40. Then, the control portion 60 detects the liquid level of the sample and stops the probe 14 in the condition that the tip of the probe 14 is inserted by about 2 mm into the sample.

Then, as shown in the diagrams (B) and (C) of FIG. 2, the control portion 60 moves down (in the direction of the arrow C) the plunger portion 23A of the diluting solution moving syringe 21. At the substantially same point of time, the control portion 60 begins to move down (in the direction of the arrow F) the plunger 32 of the sample suction syringe 30. Because the plunger portion 23B moves in the direction of the arrow C as the plunger portion 23A moves in the direction of the arrow C, the diluting solution charged in the closed flow path 10 is moved. On this occasion, the sample in the sample container 40 is sucked by the probe 14 because the plunger 32 also moves in the direction of the arrow F so that the probe 14 sucks the sample in the sample container 40. As a result, the sample is diluted in the diluting mixing pipe (in the flow path 10 between the T-junctions 12 and 16). In the embodiment shown in FIG. 1, the region X in the inside of the flow path 10 is filled with the diluted sample. The region Z in the probe 14 is filled with the undiluted sample. The region Y is a region in which the diluted sample comes into contact with the diluting solution. Hence, in the region Y, the sample is diluted at a higher rate than the original diluting rate. The magnification of dilution in the region X is determined by the ratio between the sample suction rate and the diluting solution moving rate. When, for example, the sample suction rate is 20 $\mu$l/sec and the diluting solution moving rate is 180 $\mu$l/sec, the magnification of dilution is 10.

The suction quantity Vsa of the sample suction syringe 30 on this occasion is given by the following expression (2).

$$Vsa = Va1+Va2+Va3+1/10 \cdot Vp+1/10 \cdot Vd+Vb \quad (2)$$

Accordingly, for example, the following expression is obtained.

$$Vsa = 0.8+1.2+1.4+1.9+3.0+1.256 = 9.556 \, \mu l$$

The moving quantity Vda of the diluting solution moving syringe on this occasion is given by the following expression (3).

$$Vda = 9 \cdot Va1 + 9 \cdot Vb1 + 9 \cdot Vc1 + 9 \cdot (1/10 \cdot Vd) \quad (3)$$

Accordingly, the following expression is obtained.

$$Vda = 7.2+10.8+12.6+27 = 57.6 \, \mu l$$

In this embodiment, the diluting solution moving syringes 21 and 22 of the diluting solution moving means 20 are used only for moving the diluting solution in the closed flow path 10. Only one plunger 23 is used for the diluting solution moving syringes 21 and 22, and the plunger 23 is driven by one motor 27. Hence, the diluting solution can be prevented from being delivered into the sample container 44A even in the case where the plunger 23 is stopped because of any trouble. Incidentally, the background-art method disclosed in JP-A-11-230970 has a problem that the diluting solution is delivered into the sample container if the diluting solution syringe continues to operate when the sample suction syringe is stopped because of trouble at the sample sucking time (diluting is carried out at the same time).

The operation in a period of from a point of time of 3.8 sec to a point of time of 5.0 sec will be described next.

As shown in the diagram (A) of FIG. 2, the control portion 60 moves up the probe 14 and makes it come to the washing bath 42 again. Then, as shown in the diagram (B) of FIG. 2, the control portion 60 moves up (in the direction of the arrow E) the plunger 32 of the sample syringe 30 to press the undiluted sample from the probe by the quantity Vp. On this occasion, as shown in the diagram (C) of FIG. 2, the control portion 60 moves up the plunger portion 23A of the diluting solution moving syringe 21 by 10 µl (in the direction of the arrow D). As a result, the greatly diluted sample in the region Y in the flow path 10 moves in the direction of the arrow G in the flow path 10. Hence, the periphery of the T-junction 12 can be filled with the sample diluted at a predetermined diluting rate. Hence, diluting error caused by diffusion can be reduced. The quantity of 10 µl moved by the diluting solution moving syringe 21 is a quantity contained in the dummy quantity Vd (30 µl).

The operation in a period of from a point of time of 5.0 sec to a point of time of 8.5 sec will be described next.

As shown in the diagram (A) of FIG. 2, the control portion 60 moves the probe 14 to the reaction container 44A. After the movement of the probe 14, as shown in the diagram (B) of FIG. 2, the control portion 60 moves up the plunger 32 of the sample syringe 30 to deliver the diluted solution V1 (8 µl) into the reaction container 44A. The control portion 60 further moves the probe 14 to the reaction container 44B and moves up the plunger 32 of the sample syringe 30 to deliver the diluted solution V2 (12 µl) into the reaction container 44B. The control portion 60 further moves the probe 14 to the reaction container 44C and moves up the plunger 32 of the sample syringe 30 to deliver the diluted solution V3 (14 µl) into the reaction container 44C. Thus, the operation of dispensing the sample into the three reaction containers 44A, 44B and 44C is completed.

The operation in a period of from a point of time of 8.5 sec to a point of time of 10.0 sec will be described next.

As shown in the diagram (A) of FIG. 2, the control portion 60 returns the probe 14 to the position of the washing bath 42. While the control portion 60 opens the electromagnetic valves 50, 52 and 54 as shown in the diagram (D) of FIG. 2, the control portion 60 moves up both the plunger 32 of the sample syringe 30 and the plunger portion 23A of the diluting solution moving syringe as shown in the diagram (C) of FIG. 2. The moving quantity of the plunger 32 is the quantity by which the dummy diluted sample remaining in the flow path 10 (in the diluting mixing chamber) between the T-junctions 12 and 16 is discharged. That is, the quantity is the quantity of restoration to the origin. Further, the plunger portion 23A moves up the quantity of restoration to the origin. Hence, the diluting solution is discharged from the tip of the probe 14. Hence, the flow path 10 is washed so that the solution in the flow path 10 is entirely replaced with the diluting solution. Thus, there can be made a preparation for dispensing another sample.

The accuracy of the diluting rate obtained in the dispensing apparatus according to this embodiment will be described specifically.

As described above in the expression (2), when, for example, the quantity Vsa of suction of the sample suction syringe is about 10 µl (9.556 µl), the diameter of the plunger 32 of the sample syringe 30 is selected to be 2 mmø.

On the contrary, in the background-art method described in JP-A-11-230970, the sample syringe needs to suck a predetermined amount of the sample in addition to the diluting solution fed by the diluting syringe. Accordingly, in the background-art method, the size (flow quantity) of the sample syringe is larger than that of the diluting syringe. For example, the sample syringe needs the size as obtained by addition of the moving quantity Vda (about 60 µl) of the diluting solution moving syringe to the suction quantity Vsa (about 10 µl). Hence, assuming now that the diameter of the plunger of the sample syringe according to this embodiment is 2 mmø as described above, then the diameter of the plunger of the sample syringe in JP-A-11-230970 needs to be about 5 mmø.

Therefore, the diameter of the plunger in the first syringe pump 27 in JP-A-11-230970 is selected to be 5.38516 mmø and the diameter of the plunger in the second syringe pump 28 is selected to be 5.00000 mmø. On the other hand, the diameter of the plunger of the sample syringe 30 according to this embodiment is selected to be 2.00000 mmø.

The aforementioned plunger diameters satisfy the following expression with respect to the sectional areas of the two.

$$\pi \times (2.00000)^2/4 = \pi \times \{(5.38516)^2 - (5.00000)^2\}/4$$

In other words, the plunger diameters are assumed so that the aforementioned expression holds with respect to the sectional areas of the two.

Assume now that the production error of each plunger diameter is in a range of ±0.01 mm. The accuracy of each sectional area is calculated as follows. The sectional area of a plunger having a diameter of 2 mmø is 3.14159 mm$^2$ ($=\pi \times (2.0000)^2/4$). This sectional area is used as a reference sectional area.

In this embodiment, the sectional area of a plunger is maximized when the production error of the diameter of the plunger is +0.01 mm. This sectional area is 3.17308 mm$^2$ ($=\pi \times (2.01000)^2/4$). Accordingly, the accuracy is 101.05%. The sectional area of the plunger is minimized when the production error of the diameter of the plunger is −0.01 mm. This sectional area is 3.11025 mm$^2$ ($=\pi \times (1.99000)^2/4$). Accordingly, the accuracy is 99.00%.

On the other hand, in the case disclosed in JP-A-11-230970, when the production error of the diameter of a large plunger is +0.01 mm and the production error of the diameter of a small plunger is −0.01 mm, the difference between sectional areas of the plungers is maximized. The difference between the sectional areas is 3.303325 mm$^2$ ($=\pi \times \{(5.39516)^2 - (4.99000)^2\}/4$). Accordingly, the accuracy is 105.2%. The difference between sectional areas is minimized when the production error of the diameter of a large plunger is −0.01 mm and the production error of the diameter of a small plunger is +0.01 mm. In this case, the difference between the sectional areas is 2.98129 mm$^2$ ($=\pi \times \{(5.37516)^2 - (5.01000)^2\}/4$). Accordingly, the accuracy is 94.9%.

That is, in this embodiment, dispensing error can be not larger than 1.0% when the production error of the diameter of the plunger is in a range of ±0.01 mm. On the contrary, in the case of the JP-A-11-230970, error reaches 5.2%. Accordingly, in this embodiment, dispensing accuracy is improved.

Incidentally, the cylindricity of the plunger may be put into question. The cylindricity is, however, ignorable because the production error thereof is in a range of ±0.002 mm and small and because the square of the production error concerns the sectional area of the plunger.

Further, in this embodiment, the diluted sample solution is discharged by the sample syringe having a small-diameter plunger. Accordingly, both accuracy and reproducibility in the quantity of delivery of the diluted solution are improved.

As described above, in accordance with this embodiment, both suction of the sample and dilution of the sample can be made simultaneously without necessity of any diluting cycle time. Moreover, accuracy both in the diluting rate and in the quantity of dispensing of the diluted sample can be improved.

Moreover, the serious trouble in which the diluting solution is delivered into the sample container when the sample is sucked can be prevented.

The configuration and operation of a dispensing apparatus according to a second embodiment of the present invention will be described below with reference to FIG. 3.

Figure 3:
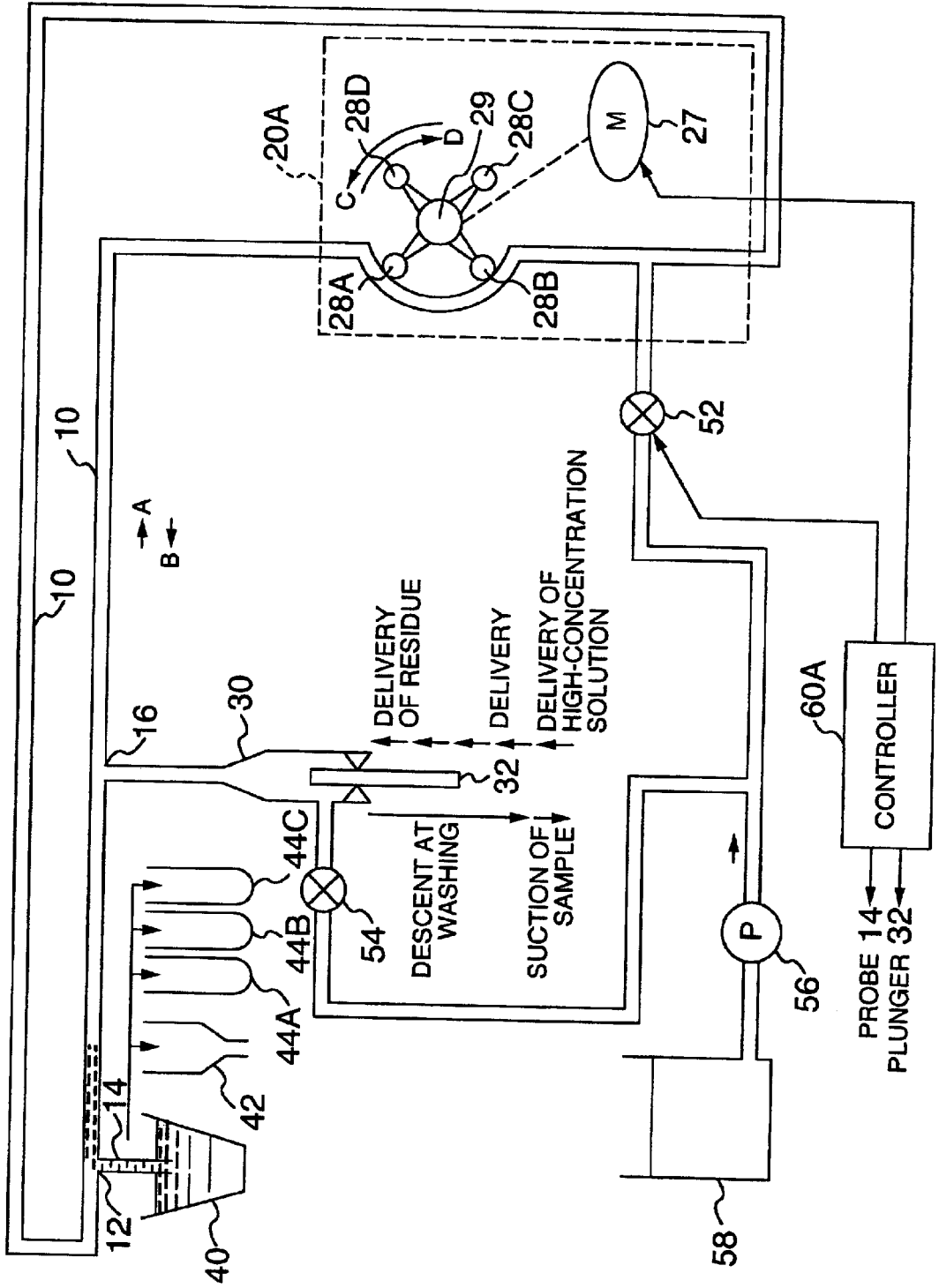
FIG. 3 is a system block diagram showing the configuration of a dispensing apparatus according to a second embodiment of the present invention.

FIG. 3 is a system block diagram showing the configuration of the dispensing apparatus according to the second embodiment of the present invention. Incidentally, in FIGS. 1 and 3, the same numerals refer to the same parts.

The end portions of the flow path 10 are connected to a diluting solution moving means 20A to thereby form a closed flow path. The diluting solution moving means 20A moves the diluting solution in the flow path 10 in forward and reverse directions, that is, in the direction of the arrow A and in the direction of the arrow B opposite to the direction of the arrow A. As will be described later, when a sample is introduced into the flow path 10, the introduced sample is diluted with a diluting solution to thereby form a diluted sample solution. The diluted sample solution is also moved in the flow path 10 by the diluting solution moving means 20A. In this embodiment, the diluting solution moving means 20A has a drive motor 27, and a wiper tube pump 29 which has rollers 28A, 28B, 28C and 28D driven to rotate by the drive motor 27. The wiper tube pump 29 is driven to rotate in the directions of the arrows C and D when the drive motor 27 is operated. When the pump 29 moves in the direction of the arrow C, the rollers 28A and 28B squash the tube which forms the flow path 10. When the squashed portion of the tube is moved, the solution in the inside of the tube is moved in the direction of the arrow A. Similarly, when the pump 29 moves in the direction of the arrow D, the solution in the inside of the tube is moved in the direction of the arrow B.

A control portion 60A controls the forward rotation, reverse rotation and suspension of the drive motor 27, reciprocating motion of the plunger 32, opening and closing of the electromagnetic valves 50 and 52 and horizontal and vertical movement of the probe 14.

The sample diluting operation in this embodiment is the same as that described above with reference to FIG. 2. In accordance with this embodiment, both suction of the sample and dilution of the sample can be made simultaneously without necessity of any diluting cycle time. Moreover, accuracy both in the diluting rate and in the quantity of dispensing of the diluted sample can be improved.

Moreover, the serious trouble in which the diluting solution is delivered into the sample container when the sample is sucked can be prevented.

What is claimed is:

1. A dispensing apparatus comprising: a flow path which forms a closed loop for making a diluted sample solution, wherein said flow path is filled with a diluting solution;
    a diluting solution moving means for moving said diluting solution in said flow path in forward and reverse directions;
    a probe connected to said flow path through a junction and a sample syringe connected to said probe through said flow path capable of sucking a sample into said flow path and delivering a sample from said flow path; and
    a control means, wherein said control means is for controlling that;
        (a) when a sample is sucked by use of said probe, said sample syringe is driven to make said probe suck said sample into said flow path and said diluting solution moving means is driven to make said diluting solution in said flow path move in forward and reverse directions, thereby said sample sucked by said probe is diluted by said diluting solution moving in said flow path; and
        (b) when a sample is delivered from said probe, said sample syringe is driven to deliver a diluted sample solution diluted by said diluting solution from said probe to a reaction container.

2. A dispensing apparatus according to claim 1, prior to delivering of said diluted sample solution from said probe, said control means controls said diluting solution moving means to move said diluting solution in said flow path in a direction opposite to a direction of movement of said diluting solution in said (a) of claim 1.

3. A dispensing apparatus according to claim 1, further comprising a washing bath, wherein
    said control means performs control so that said sample syringe is operated to deliver a high-concentration sample out of said probe into a washing bath before the diluted sample solution is discharged from said probe by said sample syringe.

4. A dispensing apparatus according to claim 1, wherein said diluting solution moving means includes:
    a first syringe connected to an end portion of said flow path;
    a second syringe connected to the other end portion of said flow path; and
    a drive means for driving plungers of said first and second syringes; wherein
        said first and second syringes operate so that said second syringe discharges said diluting solution in said flow path when said first syringe sucks said diluting solution in said flow path, and that said second syringe sucks said diluting solution in said flow path when said first syringe discharges said diluting solution in said flow path, the quantity of suction by said first syringes being equal to the quantity of delivery by said second syringe.

5. A dispensing apparatus according to claim 4, wherein said plungers in said first and second syringes are combined with and are driven by a motor.

6. A dispensing apparatus according to claim 1, wherein a portion of said flow path comprises a tube, wherein further said diluting solution moving means includes:
    a plurality of rollers for squashing said tube connected to opposite ends of said flow path; and
    a drive means for driving said rollers to rotate in forward and reverse directions.

7. A sample dispensing method in which a sample is sucked from a sample container into dispensing probe capable of moving up and down and delivering said sucked sample into reaction containers, a flow path which forms a closed loop for making a diluted sample solution in said flow path filled with a diluting solution, the sample dispensing method comprising the steps of:
    driving a diluting solution moving means to make said diluting solution move in said flow path, and driving a sample syringe connected to a probe and said flow path through a junction to suck a sample into said flow path through said probe;
    driving said diluting solution moving means to make said diluting solution in said flow path move in forward and reverse directions, thereby causing said sample sucked by said probe to become diluted by said diluting solution moving in said flow path; and
    driving said sample syringe so that said diluted sample solution diluted with said diluting solution is delivered from said probe into said reaction containers.

* * * * *